US005826573A

United States Patent [19]

Stegmann et al.

[11] Patent Number: 5,826,573

[45] Date of Patent: Oct. 27, 1998

[54] GAS FLOW CONTROL ELEMENT

[75] Inventors: Holger Stegmann, Lübeck; Eckhard Riggert, Ratekau, both of Germany

[73] Assignee: Drägerwerk AG, Lübeck, Germany

[21] Appl. No.: 856,130

[22] Filed: May 14, 1997

[30] Foreign Application Priority Data

Nov. 7, 1996 [DE] Germany ........................ 196 45 941.9

[51] Int. Cl.$^{6}$ ............................ A61M 16/00; A62B 7/00; B01D 19/00; F01M 7/08

[52] U.S. Cl. ................................ 128/200.24; 128/202.13; 128/204.18; 55/276; 181/258

[58] Field of Search ......................... 128/204.18, 200.24, 128/202.13; 55/276; 181/242, 248, 252, 224, 227, 241, 247, 267, 258

[56] References Cited

U.S. PATENT DOCUMENTS

| | | | |
|---|---|---|---|
| 4,134,472 | 1/1979 | Trainor | 181/258 |
| 4,644,947 | 2/1987 | Whitwam et al. | 128/207.16 |
| 4,751,980 | 6/1988 | DeVane | 181/239 |
| 5,152,366 | 10/1992 | Reitz | 181/249 |
| 5,663,537 | 9/1997 | Ko et al. | 181/228 |

FOREIGN PATENT DOCUMENTS

| | | |
|---|---|---|
| 0 360 044 B1 | 8/1989 | European Pat. Off. . |

*Primary Examiner*—Kimberly L. Asher
*Attorney, Agent, or Firm*—McGlew and Tuttle

[57] ABSTRACT

A gas flow control element with a gas-permeable section, through which excess gas flows to the outside from an interior space (10), is to be improved such that it can be cleaned with ease and that a defined, reproducible discharge is present. To accomplish this task, the gas-permeable section comprises individual disks (5) lying one on top of another, which are provided with flow channels.

19 Claims, 3 Drawing Sheets

GAS FLOW CONTROL ELEMENT

FIELD OF THE INVENTION

The present invention pertains to a gas flow control element with a gas-permeable section, through which excess gas flows to the outside from an interior space of the gas flow control element.

BACKGROUND OF THE INVENTION

A gas flow control element of this type has become known from EP 360 044 B1. The prior-art gas flow control element comprises a corrugated tube, which is provided with circumferential perforations, which are covered by a mat of sound-reducing material. The noise reduction is achieved due to the special design of the circumferential perforation in conjunction with the selection of the material of the mat. However, mats made of sound-reducing material are inexpedient for applications in which frequent cleaning of the gas flow control element is necessary, because dirt particles can be removed from the interior of the mat with difficulty only. The flow resistance of the mat increases in the course of the use time as a result. In addition, a defined porosity, which is decisive for the efficiency of the sound reduction, is difficult to obtain with the prior-art sound-reducing material.

SUMMARY AND OBJECTS OF THE INVENTION

The primary object of the present invention is to improve a gas flow control element of the type such that it can be cleaned with ease and a defined, reproducible pore size is present.

This object is accomplished by the gas-permeable section of the gas flow control element consisting of individual disks located one on top of another or one adjacent to another, which are provided with flow channels.

The advantage of the present invention is essentially that defined flow conditions are established by a package of disks, which are located one on top of another or one adjacent to another and which are provided with individual flow channels, because the discharge area available is set by the number of flow channels and the cross-sectional area of the flow channels. The flow channels may be designed as, e.g., holes extending through the disks. A defined pressure drop and volume flow can be set between the interior space of the gas flow control element and the environment in a particularly simple manner by selecting the number of flow channels per disk and the number of disks lying one on top of another.

It is especially advantageous for the flow channels to be designed as radially extending, groove-like depressions in the surface of the disks. It is especially expedient in this connection to arrange the flow channels on both sides of the disk surface. A further improvement is achieved by a spiral course of the flow channels, in which case the channels are directed in opposite directions on the respective disk surfaces. A degressive increase in volume flow with increasing pressure is thus achieved.

The number of flow channels is advantageously greater than or equal to 500 in the area of the gas-permeable section, the cross-sectional area of one flow channel being larger than 0.01 $mm^2$. The preferred number of flow channels is in a range of 800 to 1,200, with a cross-sectional area per channel greater than 0.01 $mm^2$ and preferably 0.024 $mm^2$.

It is especially advantageous to use the gas flow control element according to the present invention in a respirator, because the degressive increase in volume flow can be utilized in an especially advantageous manner here. Suitable respirators are, e.g., so-called single-tube devices, in which a certain gas flow is continuously delivered to a patient by means of a fan via a breathing tube and the gas flow control element. The exhaled gas flows back into the breathing tube and is blown off into the environment via the gas-permeable section.

One exemplary embodiment of the present invention is shown in the figure and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
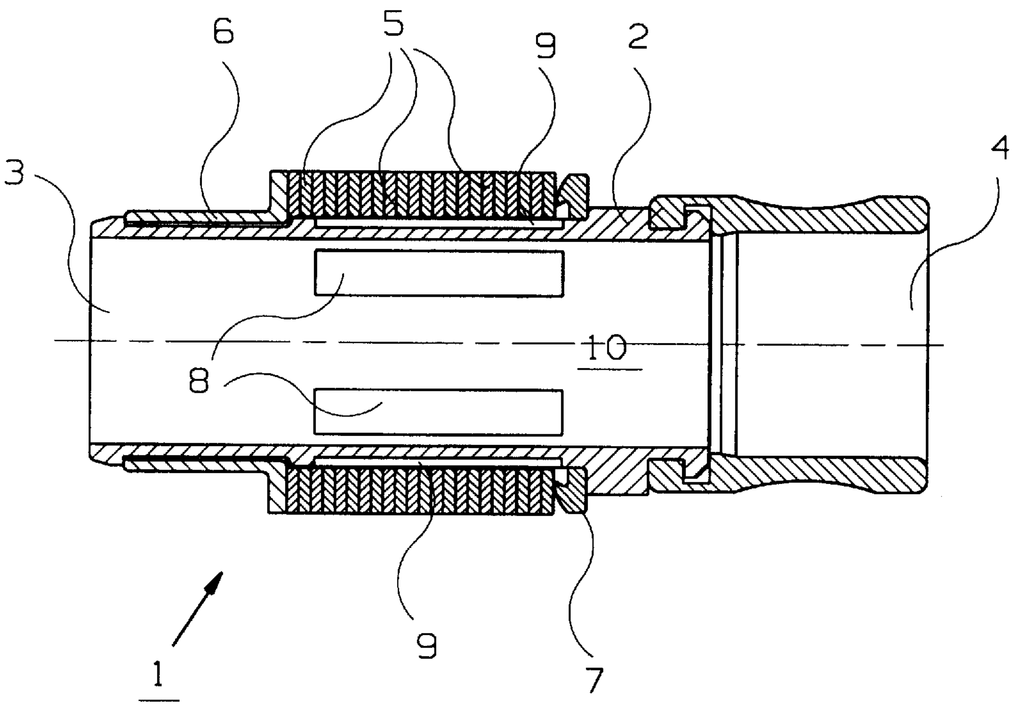
FIG. 1 is the longitudinal sectional view of a gas flow control element according to the invention.

Referring to the drawings in particular, FIG. 1 shows the longitudinal section of a gas flow control element 1, which comprises essentially a cylindrical tube (or flow content) 2 with a gas inlet 3 and a gas outlet 4 and individual disks 5 placed on the tube 2. The number of disks 5 is decisive for the volume flowing off. The disks 5, 22 disks in this case, are fastened to the tube 2 by means of a clamping sleeve 6 and an abutment 7. Individual openings or perforations 8, which open into a gas distribution space 9, are arranged in the tube 2 in the overlapping area between the disks 5 and the tube 2. The gas present in the interior space 10 of the tube 2 flows through the perforations 8 into the gas distribution space 9 and into the environment through the disks 5.

Figure 2:
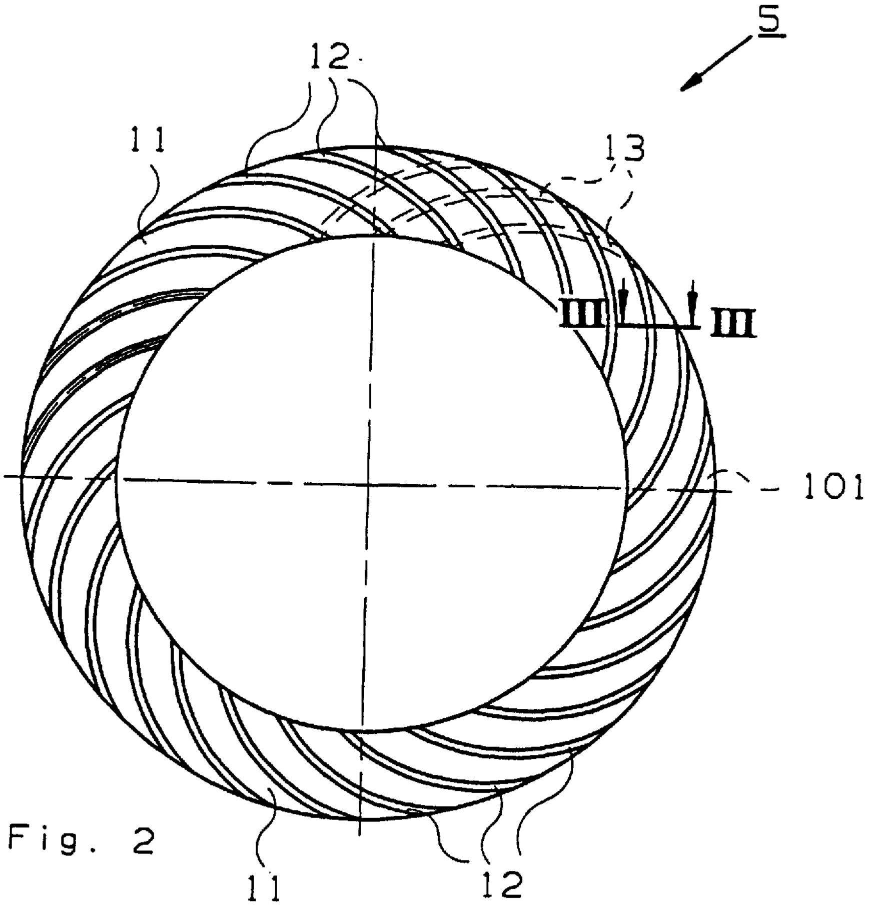
FIG. 2 is a top view of a disk of the gas flow control element.

FIG. 2 shows a top view of one of the disks 5. The disks 5 have a flat disk surface 11, in which spiral, radially extending grooves 12 are provided at equidistant locations as flow channels. Grooves (opposite side grooves) 13 extending in the opposite direction in a corresponding manner are provided as flow channels on the reverse side of the disk 5 in a disk surface 101. The disk surfaces 11, 101 are plane-parallel in relation to one another, and the disk surface 101 is not visible in FIG. 2. The grooves 13 are therefore indicated by broken lines in FIG. 2, and only three of the grooves 13 are shown for the sake of greater clarity.

Figure 3:
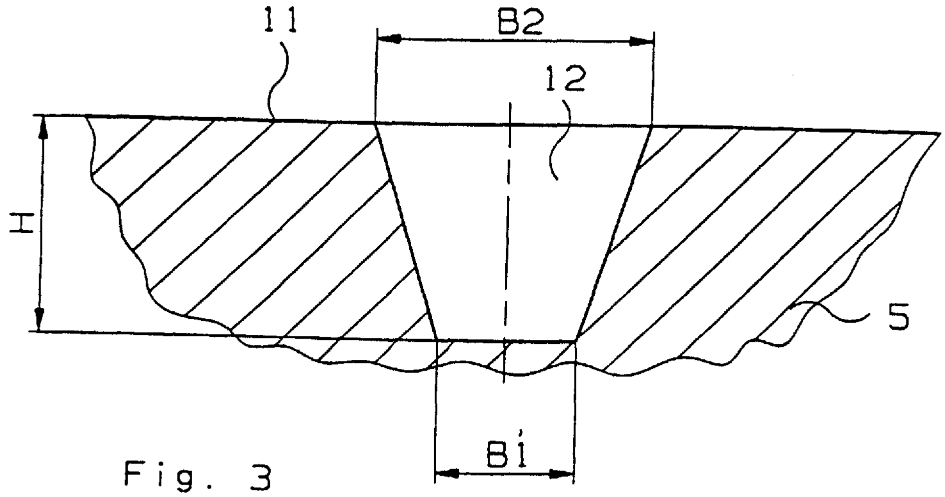
FIG. 3 is a sectional broken away view A—A of a groove within the disk according to FIG. 2.

FIG. 3 shows a sectional broken away view of one of the grooves 12 along the section line A—A in FIG. 2. The groove 12 has an essentially trapezoidal cross-sectional contour with a first trapezoid width B1 of about 0.1 mm, a second trapezoid width B2 of 0.2 mm, and a trapezoid height H of 0.16 mm. Other cross-sectional contours of the groove 12 are also possible, e.g., a rectangular cross section or a triangular shape, which lead to equally good results. A cross-sectional area of 0.024 $mm^2$ for the groove 12 proved to be particularly advantageous. The groove 13 is designed corresponding to the groove 12. There are 24 grooves 12, 13 each on each of the disk surfaces 11, 101 of the disk 5. The external diameter of the disk 5 is about 29 mm, and the internal diameter is about 21 mm. A diffuse discharge with minimized noise is achieved due to the disks 5 with the grooves 12, 13, which disks are assembled in a package, and a defined discharge from the interior space 10 is achieved due to the geometry of the grooves 12, 13. To clean the gas flow control element 1, the clamping sleeve 6 is loosened, so that the disks 5 can be removed from the tube 2. By taking apart, the disks 5 can be cleaned individually especially well. The gas flow control element 1 according to the present invention can be used especially advantageously for the artificial respiration of a patient with a fan-operated respirator 20 by connecting a breathing tube 22, (shown in FIG. 4), which is connected to the fan, to the gas inlet 3. The gas outlet 4 is connected vis a line 24 to a breathing mask 26, which is likewise shown in FIG. 4. A possibly degressive change in the volume V being discharged as a function of the pressure p in the interior space 10 is desirable in the respiration technique for the discharge of the breathing gas through the grooves 12, 13 of the disks 5. Since the respirator is a so-called single-tube device in this case, in which the patient breathes back into the breathing tube, the carbon dioxide exhaled must be blown off into the environment via the grooves 12, 13. The purging of carbon dioxide via the grooves 12, 13 is, in general, not critical at higher respiration pressures, so that the gas flow being discharged via the grooves 12, 13 does not have to increase linearly with the pressure. In contrast, too much gas would be discharged via the grooves 12, 13 in the case of a linear relationship between the pressure p and the volume V. The degressive change in the volume V being discharged as a function of the pressure p is achieved in the gas flow control element 1 according to the present invention by the spirally arranged grooves 12, 13, which are directed in opposite directions. The degressive shape of the curve can be attributed essentially to the fact that turbulences, which bring about a greater than proportional increase in the flow resistance offered by the disks 5, are generated in the grooves 12, 13 between adjacent disks 5 as a consequence of the crossing air flows.

Figure 4:
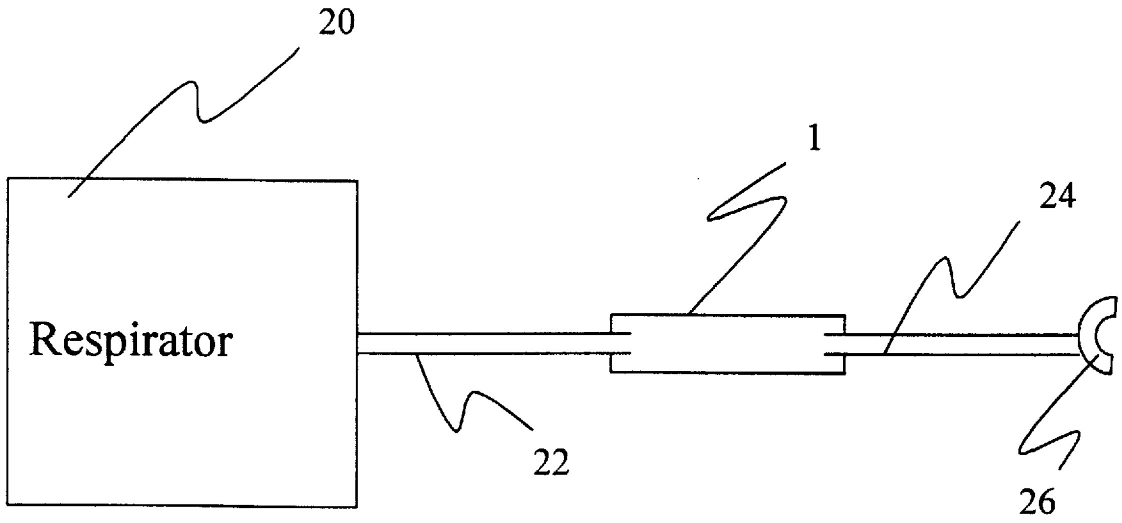
FIG. 4 is a schematic view showing the gas flow control element connected in a breathing line of a respirator.

FIG. 4 is a schematic representation showing the fan operated respirator 20 with breathing tube portions 22 and 24. Breathing tube portion 22 connects to the fan operated respirator 20 and connects into the inlet end 3 of the gas flow control element 1. The breathing line portion 1 connects the outlet 4 of the gas flow control element 1 to the breathing mask (or other similar patient/user connection) 26.

While specific embodiments of the invention have been shown and described in detail to illustrate the application of the principles of the invention, it will be understood that the invention may be embodied otherwise without departing from such principles.

What is claimed is:

1. A gas flow control element, comprising:

a gas-permeable section through which excess gas flows to an outside of said gas-permeable section from an interior space of the gas flow control element, said gas-permeable section including individual disks lying one adjacent to another, said individual disks having flow channels, wherein said flow channels are radially extending, groove-like depressions in a surface of said individual disks.

2. The gas flow control element in accordance with claim 1, wherein said flow channels are present on both side surfaces of each of said individual disks.

3. The gas flow control element in accordance with claim 1, wherein said flow channels have a spiral course.

4. The gas flow control element in accordance with claim 1, wherein said channels on said disk surfaces extend in opposite directions.

5. The gas flow control element in accordance claim 1, wherein a number of said flow channels in an area of said gas-permeable section is greater than 500.

6. The gas flow control element in accordance with claim 1, wherein said cross-sectional area of one said flow channel is greater than 0.01 $mm^2$.

7. A process for providing gas flow control, comprising the steps of:

providing a tube having an interior space, an inlet, an outlet and a peripheral surface with openings through which excess gas flows from said interior space of said tube;

providing a plurality of disks lying one adjacent to another around said peripheral surface of said tube, at least some of said disks defining radial flow channels from a region adjacent to said openings to an outside, said radial flow channels being formed as groove-like depressions in a surface of each of said some individual disks;

providing said tube and said disks as a control element within a gas flow of a respirator.

8. The process for providing gas flow control according to claim 7, further comprising the steps of:

providing the radial flow grooves as groove-like depressions in a surface of each of said individual disks; and providing said individual disks with opposite side radial flow grooves including groove-like depressions in an opposite surface of each of said individual disks, said opposite side radial flow grooves cooperating with an adjacent disk to define opposite side flow channels, wherein said flow channels and said opposite side flow channels are curved and said flow channels of one of said disks crosses said opposite side flow channels of an adjacent another of said disks to define turbulence zones based on crossing air flows, said turbulence zones effecting an increase of flow resistance through said flow channels and said opposite side flow channels.

9. The process for providing gas flow control according to claim 7, further comprising the steps of:

providing clamping means for fixing said plurality of disks one adjacent to another around said periphery of said tube.

10. A gas flow control device, comprising:

a flow conduit with a gas flow inlet and a gas flow outlet, said flow conduit defining an interior space, said flow conduit having a peripheral surface with openings;

a plurality of disks lying one adjacent to another, at least some of said disks having generally radial flow grooves formed as groove-like depressions in a surface of each of said some individual disks, extending from adjacent to said peripheral surface with openings to an outside of the gas flow control device, said radial flow grooves cooperating with an adjacent disk to define flow channels.

11. The device in accordance with claim 10, wherein each of said individual disks includes opposite side radial flow grooves including groove-like depressions in an opposite surface of each of said individual disks, said opposite side radial flow grooves cooperating with an adjacent disk to define opposite side flow channels.

12. The device in accordance with claim 10, wherein said flow channels and said opposite side flow channels are curved and said flow channels of one of said disks crosses said opposite side flow channels of an adjacent another of said disks to define turbulence zones based on crossing air flows, said turbulence zones effecting an increase of flow resistance through said flow channels and said opposite side flow channels.

13. The device in accordance with claim 10, further comprising clamping means for fixing said plurality of disks one adjacent to another around said periphery of said tube.

14. The device in accordance with claim 13, wherein said clamping means comprises: an abutment in contact with one of said plurality of disks at an end of said plurality of disks; and a clamping sleeve in contact with one of said plurality of disks at another end of said plurality of disks.

15. The device in accordance with claim 10, wherein said flow channels have a spiral course.

16. The device in accordance with claim 10, wherein said flow channels on said disk surfaces extend in opposite directions.

17. The device in accordance claim 10, wherein a number of said flow channels in an area of said gas-permeable section is greater than 500.

18. The device in accordance with claim 10, wherein said cross-sectional area of one said flow channel is greater than 0.01 $mm^2$.

19. The device in accordance with claim 10, further comprising a respirator connected to said gas flow control element.

* * * * *